United States Patent [19]

Malen et al.

[11] Patent Number: 4,567,181

[45] Date of Patent: Jan. 28, 1986

[54] BICYCLO (4.2.0) 1,3,5-OCTATRIENE COMPOUNDS AND USE AS α-ADRENERGICS

[75] Inventors: Charles Malen, Fresnes; Jean-Louis Peglion, Chatou; Michel Laubie, Vaucresson; Jean-Claude Poignant, Bures s/Yvette, all of France

[73] Assignee: ADIR, S.A.R.L., Neuilly-sur-Seine, France

[21] Appl. No.: 596,932

[22] Filed: Apr. 5, 1984

Related U.S. Application Data

[63] Continuation-in-part of Ser. No. 570,529, Jan. 13, 1984, abandoned.

[51] Int. Cl.⁴ .................. A61K 31/505; A61K 31/415; C07D 239/02; C07D 233/04
[52] U.S. Cl. ...................................... 514/256; 544/335; 544/242; 544/333; 548/353; 548/347; 548/348; 514/401; 514/402
[58] Field of Search ....................... 544/335, 242, 333; 548/353, 347, 348; 424/251, 273 R; 514/256, 401, 402

[56] References Cited

U.S. PATENT DOCUMENTS 4,226,876  10/1980  Copp et al. ........................... 548/353

OTHER PUBLICATIONS

The Pharmacological Basis of Therapeutics, Gilman Goodman, and Gilman, Sixth Edition, pp. 184, 185, 186, and p. 793.

Physician's Desk Reference, 38th Edition (1984), p. 1558.
Science 199, Jan. 13, 1978, pp. 197–198.
The New England Journal of Medicine, Sep. 1, 1977, pp. 476–482.
Life Sciences 21, 1977, pp. 595–606 (Pergamon Press).

Primary Examiner—Henry R. Jiles
Assistant Examiner—Robert C. Whittenbaugh
Attorney, Agent, or Firm—Gordon W. Hueschen

[57] ABSTRACT

Compounds of the formula:

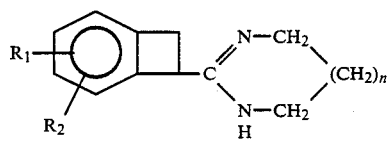

in which:
$R_1$ and $R_2$ each represent, independently of one another, hydrogen, halogen, alkyl or alkoxy having from 1 to 4 carbon atoms, sulphonamide possibly substituted by an alkyl radical having from 1 to 4 carbon atoms; or together methylenedioxy, n is 0 or 1,
in racemic form or in the form of optical isomers, and also their salts of addition with pharmaceutically acceptable acids. Useful in the treatment of ailments and/or conditions which are adrenoreceptor-related, such relationship being well known in the art.

8 Claims, No Drawings

BICYCLO (4.2.0) 1,3,5-OCTATRIENE COMPOUNDS AND USE AS α-ADRENERGICS

This application is a continuation in part of our prior-filed co-pending application, Ser. No. 570,529, filed Jan. 13, 1984, now abandoned.

The present invention relates to bicyclo[4.2.0]1,3,5-octatriene compounds, methods for preparing them and pharmaceutical compositions containing them.

The compounds of the invention correspond to the general formula:

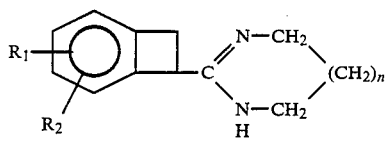

in which:
$R_1$ and $R_2$ which are the same or different are selected form the group consisting of a hydrogen atom, a halogen atom, alkyl and alkoxy radicals each having from 1 to 4 carbon atoms inclusive, a sulphonamide radical possibly substituted by an alkyl radical having from 1 to 4 carbon atoms; and they together represent a methylene-dioxy radical,
n is selected from the group consisting of 0 and 1,
in racemic form and in the form of optical isomers, and also their salts of addition to pharmaceutically acceptable acids.

The compounds according to the invention have an asymmetric carbon atom and they can therefore be resolved into their optical isomers. The addition salts are obtained with pharmaceutically acceptable mineral or organic acids, such as hydrochloric acid, sulphuric acid, methanesulphonic acid, tartaric acid, citric acid, fumaric acid, maleic acid, etc . . . .

Of the compounds of the invention, those that are preferred correspond to the formula I in which $R_1$ and $R_2$ each represent a hydrogen atom.

The compounds of the invention may be prepared by condensing in the presence of $H_2S$, a derivative of the general formula II:

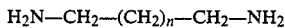

in which n has the same meaning as in formula I, with a compound of the general formula III:

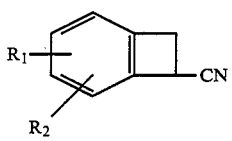

in which $R_1$ and $R_2$ have the same meanings as in formula I.

This reaction may be advantageously carried out at ambient temperature or by moderate heating. It is also possible to use an inert solvent such as methanol, ethanol, or propanol.

The optical isomers of the compounds of the invention may be separated in conventional manner after formation of a salt with an optically active acid, such as tartaric acid, and fractional crystallisation of the tartrates obtained, and then, if desired, liberation of the optically active base by means of a strong base (or transsalification by means of a strong acid). However, the optically active bases can readily racemise and it is more advantageous to keep the enantiomers in the form of their addition salts, which are generally stable in the solid state.

The compounds of the general formula III are generally known in the literature, but on the other hand, those in which $R_1$ represents a hydrogen atom and $R_2$ represents a chlorine atom in position -2 or -3, a fluorine atom in position -4 or a sulphonamide in position -4 are new and are prepared according to the prior art and as disclosed hereinafter.

Certain bicyclo octatrienes (tetrahydrozoline) substituted by a 2-imidazolinyl group are known in the literature (U.S. Pat. No. 2,731,471 of Sahyun and U.S. Pat. No. 2,842,478 of Pfizer) and have an α-adrenergic agonist activity which justifies, in particular, their therapeutic use as vasoconstrictors and nasal decongestants.

The compounds of the invention have a bicyclo[4.2.0]1,3,5-octatrienic structure substituted by a 2-imidazolinyl group, but they show completely opposite effects, as they are α-adrenergic antagonists.

Other heterocyclic compounds substituted by an imidazoline are known in the literature (Pat. No. EP 71.368 of Reckitt and Colman) and also show an α-adrenergic antagonist activity.

But the compounds of the invention are particularly distinguished by the nature of their cycle and by the selectivity of their isomers on $\alpha_1$ or $\alpha_2$ receptors, which allows their use in different therapeutic indications.

The following examples illustrate the preparation of the compounds of the invention. The melting temperatures (°C.) were measured on a "Micro-Kofler" block.

EXAMPLE 1

(d,l) 7-(2-imidazolinyl) bicyclo[4.2.0]1,3,5-octatriene 5 g of 7-yano bicyclo[4.2.0]1,3,5-octatriene (prepared according to the method described in Org. Synth. Coll., Vol. V, p. 263), and then 7.2 g of 1,2-diamino ethane are introduced into a vessel and the whole is saturated with $H_2S$ with the exclusion of moisture. After four days of contact, with intermittent agitation of the pasty mass formed, 30 cm$^3$ of water are added and the whole is rendered alkaline with sodium hydroxide and extracted with methylene chloride. The extract is washed with water, dried and the solvent is evaporated. The racemic 7-(2-imidazolinyl)bicyclo[4.2.0]1,3,5-octatriene is obtained
either as a base by distillation of the residue at 120°/0.02 mm Hg and recrystallisation into ethyl acetate
or as converted into the hydrochloride.
m.p.=102°–107° (base); 180°–190° (hydrochloride) with decomposition.
Analysis (base)
NMR: (2H) 3.4 ppm; (4H) 3.5 ppm, (S); (1H exchangeable) 6.2 ppm; (1H) 6.3 ppm; (4H Aromatics) 7.2 ppm.
IR: NH: 3220 cm$^{-1}$. C≡N: 1610 cm$^{-1}$.

EXAMPLE 2

(−)-tartrate of 7-(2-imidazolinyl)bicyclo[4.2.0]1,3,5-octatriene 8 g of the 7-(2-imidazolinyl)bicyclo[4.2.0]1,3,5-octatriene obtained above and 6.9 g of (+)-tartaric acid are dissolved and boiled in 30 ml of ethanol.

The residue is taken up in 50 ml of isopropanol and evaporated to dryness. After recrystallising five times the (−)-tartrate of 7-(2-imidazolinyl)bicyclo[4.2.0]1,3,5-octatriene is obtained:

m.p.=155°–160°.

$[\alpha]_{589}^{22} = -61.7$. $[\alpha]_{365}^{22} = -218$ (0.5% H$_2$O).

EXAMPLE 3

(+)-tartrate of 7-(2-imidazolinyl)bicyclo[4.2.0]1,3,5-octatriene

By replacing the (+)-tartaric acid of Example 2 with (−)-tartarate acid, the (+)-tartaric of 7-(2-imidazolinyl)bicyclo[4.2.0]1,3,5-octatriene is obtained in the same manner.

m.p.=155°–160°.

EXAMPLE 4

3-methoxy 7-(2-imidazolinyl)bicyclo[4.2.0]1,3,5-octatriene 9.6 g of 3-methoxy 7-cyano bicyclo[4.2.0]1,3,5-octatriene (described in *J. Am. Chem. Soc.*, 98 (11), p. 3378-9 (1976)) are dissolved in 10.8 g of 1,2-diamino ethane. The solution is saturated with H$_2$S while maintaining the temperature at 0° C., then after one night at ambient temperature, the mixture is heated for 18 hours at 50° C. After cooling, diluted sodium hydroxide is added and the solution is extracted with methylene chloride. The organic phase is taken up and extracted with a 1N hydrochloric acid solution. The aqueous phase is again extracted with methylene chloride which is dried and evaporated under reduced pressure. The residue obtained is purified by treatment at ambient temperature with acetic anhydride in acetic acid, then, dilution in water, and alkalinisation by aqueous sodium hydroxide and extraction with methylene chloride.

The organic phase is washed with water, dried and evaporated under reduced pressure. After recrystallisation from acetonitrile, 6.6 g of 3-methoxy 7-(2-imidazolinyl)bicyclo[4.2.0]1,3,5-octatriene are obtained, which can be converted into the fumarate.

m.p.=128°–132° (base); 135°–139° (fumarate).

| Analysis (fumarate) | C % | H % | N % |
|---|---|---|---|
| Calculated | 60.37 | 5.70 | 8.80 |
| Found | 60.29 | 5.69 | 8.89 |
| for C$_{12}$H$_{14}$N$_2$O, C$_4$H$_4$O$_4$ = 318.33 | | | |

EXAMPLE 5

4-methoxy 7-(2-imidazolinyl)bicyclo[4.2.0]1,3,5-octatriene

Prepared according to Example 4, starting from 4-methoxy 7-cyano bicyclo[4.2.0]1,3,5-octatriene (Tetrahedron 30, p. 1053 (1979)).

m.p.=117°–120° (base); 178°–180° (fumarate).

| Analysis (fumarate) | C % | H % | N % |
|---|---|---|---|
| Calculated | 60.37 | 5.70 | 8.80 |
| Found | 60.00 | 5.66 | 8.64 |
| for C$_{12}$H$_{14}$N$_2$O, C$_4$H$_4$O$_4$ = 318.33 | | | |

EXAMPLE 6

4-chloro 7-(2-imidazolinyl)bicyclo[4.2.0]1,3,5-octatriene

Prepared according to Example 4, starting from 4-chloro 7-cyano bicyclo[4.2.0]1,3,5-octatriene (*J.AM.-CHEM.SOC.* 33 (8), 3327-9, 1968).

m.p.=127°–130° (base); 171°–174° (fumarate).

| Analysis (fumarate) | C % | H % | N % |
|---|---|---|---|
| Calculated | 55.82 | 4.68 | 8.68 |
| Found | 55.73 | 4.74 | 8.63 |
| for C$_{11}$H$_{11}$ClN$_2$, C$_4$H$_4$O$_4$ = 322.75 | | | |

EXAMPLE 7

3,4-dimethoxy 7-(2-imidazolinyl)bicyclo[4.2.0]1,3,5-octatriene

Prepared according to Example 4, starting from 3,4-dimethoxy 7-cyano bicyclo[4.2.0]1,3,5-octatriene (*Tetrahedron* 29, p.73 (1973))

m.p.=158°–161° (base); 215° (fumarate).

| Analysis (fumarate). | C % | H % | N % |
|---|---|---|---|
| Calculated | 58.61 | 5.79 | 8.04 |
| Found | 58.52 | 5.79 | 7.94 |
| for C$_{13}$H$_{16}$N$_2$O$_2$, C$_4$H$_4$O$_4$ = 348.35 | | | |

EXAMPLE 8

2-chloro 7-(2-imidazolinyl)bicyclo[4.2.0]1,3,5-octatriene

Step A:

2-cyano 3-(2,6-dichloro phenyl)propanoic acid.

92 g of 2-cyano 3-(2,6-dichlorophenyl)propenoic acid (*Tetrahedron Lett.*, 1975, p.3643-4) are put into 860 ml of methanol and 285 ml of a 10% sodium hydrogen carbonate solution. This is cooled to 18° C. and the necessary quantity of sodium borohydride is introduced over a two and one-half hour period. The mixture is left for 2 hours at ambient temperature, then concentrated and acidified by adding 1N hydrochloric acid until a pH of 2.3. The solution is then extracted with ether and the organic layer is washed with water, dried on magnesium sulphate, filtered and evaporated. 82.4 g of 2-cyano 3-(2,6-dichlorophenyl)propanoic acid are obtained.

m.p.=106°–108°.

Step B:

3-(2,6-dichlorophenyl)propionitrile.

81.3 g of 2-cyano 3-(2,6-dichlorophenyl)propanoic acid obtained above are dissolved in 140 ml of N,N dimethylaminoacetamide and heated for 1 hour at 140°–150° C. After cooling, the reaction mixture is poured into 600 ml of water, and extracted with 3200 ml of ether. The organic layer is washed with a saturated solution of sodium hydrogen carbonate, then with a saturated solution of sodium chloride. The organic phase is decolored, dried and evaporated. 61.7 g of 3-(2,6-dichlorophenyl)propionitrile are obtained in the form of an oil which crystallises at ambient temperature.

Step C:

2-chloro 7-cyano bicyclo[4.2.0]1,3,5-octatriene.

Applying the method described in Org. Synth. Coll. Vol. V, p.263 to 20 g of 3-(2,6-dichlorophenyl)propionitrile obtained above, and after distillation at 114°–118° C. under 0.05 mm Hg, 10.4 g of 2-chloro 7-cyano bicyclo[4.2.0]1,3,5-octatriene are obtained.

IR: $\nu(C\equiv N)$ band at 2240 cm$^{-1}$.

Step D:

2-chloro 7-(2-imidazolinyl)bicyclo[4.2.0]1,3,5-octatriene.

Prepared according to Example 4, starting from 2-chloro 7-cyano bicyclo[4.2.0]1,3,5-octatriene obtained in Step C above.

m.p.=100°–106° (base); 189°–196° (fumarate).

| Analysis (fumarate) | C % | H % | N % |
|---|---|---|---|
| Calculated | 55.82 | 4.68 | 8.68 |
| Found | 55.76 | 4.78 | 8.70 |
| for C$_{11}$H$_{11}$ClN$_2$, C$_4$H$_4$O$_4$ = 322.75 | | | |

EXAMPLE 9

2-chloro 7-(2-tetrahydropyrimidinyl)bicyclo[4.2.0]1,3,5-octatriene.

Prepared according to Example 4, starting from 1,3-diamino propane, and 2-chloro-7-cyano bicyclo[4.2.0]1,3,5-octatriene (Example 8, Step C).

m.p.=133°–136° (base); 185°–195° (fumarate).

| Analysis (fumarate) | C % | H % | N % |
|---|---|---|---|
| Calculated | 57.06 | 5.09 | 8.32 |
| Found | 56.81 | 5.09 | 8.32 |
| for C$_{12}$H$_{13}$ClN$_2$, C$_4$H$_4$O$_4$ = 336.77 | | | |

EXAMPLE 10

3-chloro 7-(2-imidazolinyl)bicyclo[4.2.0]1,3,5-octatriene

Step A:

3-nitro 7-cyano bicyclo[4.2.0]1,3,5-octatriene.

The nitration reaction of 7-cyano bicyclo[4.2.0]1,3,5-octatriene described in J. Org. Chem. 33(8), p.3327(1968) gives 4-nitro 7-cyano bicyclo[4.2.0]1,3,5-octatriene. Moreover, a small proportion of the nitrated compounds in position -3 can be obtained. Thus, from 77.4 g of 7-cyano bicyclo[4.2.0]1,3,5-octatriene 3.3 g of 3-nitro 7-cyano bicyclo[4.2.0]1,3,5-octatriene are obtained after chromatography of the recrystallisation mother liquors of the nitrated compounds in position -4, on a silica column (Kieselgel 60.70.230 mesh ASTM) by eluting through a mixture of cyclohexaneethylacetate (70:30). This compound is then recrystallised in pure ethanol (m.p.=73°–77°).

Step B:

3-amino 7-cyano bicyclo[4.2.0]1,3,5-octatriene.

The reduction, on Pd/C at 5% in ethanol in the presence of acetic acid, of 4.7 g of 3-nitro 7-cyano bicyclo[4.2.0]1,3,5-octatriene obtained in Step A above gives 3.3 g of 3-amino 7-cyano bicyclo[4.2.0]1,3,5-octatriene.

Chlorhydrate m.p.: 195° (decomposition).

Step C:

3-chloro 7-cyano bicyclo[4.2.0]1,3,5-octatriene.

By the Sandmeyer reaction, starting from 3.2 g of 3-amino 7-cyano bicyclo[4.2.0]1,3,5-octatriene obtained in Step B above, an oil is obtained which after distillation at 100° C. under 0.05 mm Hg gives 2.1 g of 3-chloro 7-cyano bicyclo[4.2.0]1,3,5-octatriene (n$_D^{24}$: 1.5639)

Step D:

3-chloro 7-(2-imidazolinyl)bicyclo[4.2.0]1,3,5-octatriene.

In 12 ml of anhydrous methanol 3.7 g of 1,2-diamino ethane are mixed with 2 g of 3-chloro 7-cyano bicyclo[4.2.0]1,3,5-octatriene, obtained in Step C above. The mixture is saturated with H$_2$S in maintaining the temperature at 0° C., then boiled for 4 hours.

After evaporation of the solvent, the residue is taken up in a diluted sodium hydroxide solution which is extracted with methylene chloride. After extraction of the organic phase with a 1N hydrochloric acid solution, dilution of this acid phase with an aqueous sodium hydroxide and extraction with methylene chloride, 2.1 g of 3-chloro 7-(2-imidazolinyl)bicyclo[4.2.0]1,3,5-octatriene are obtained which are recrystallised in acetonitrile.

m.p.=127°–133° (base); 149°–152° (fumarate).

| Analysis (fumarate) | C % | H % | N % |
|---|---|---|---|
| Calculated | 55.82 | 4.68 | 8.68 |
| Found | 55.55 | 4.62 | 8.57 |
| for C$_{11}$H$_{11}$ClN$_2$, C$_4$H$_4$O$_4$ = 322.75 | | | |

EXAMPLE 11

4-fluoro 7-(2-imidazolinyl)bicyclo[4.2.0]1,3,5-octatriene

Step A:

4-fluoro 7-cyano bicyclo[4.2.0]1,3,5-octatriene.

By applying the conditions of the SCHIEMANN reaction to 14.4 g of 4-amino 7-cyano bicyclo[4.2.0]1,3,5-octatriene prepared according to the method described in J. Org. Chem., 33(8), p.3327(1068), 3.2 g of brown oil are obtained, which, after distillation at 125° C. under 0.05 mm Hg, gives 1.4 g of 4-fluoro 7-cyano bicyclo[4.2.0]1,3,5-octatriene (n$_D^{25}$=1.5082).

Step B:

4-fluoro 7-(2-imidazolinyl)bicyclo[4.2.0]1,3,5-octatriene.

4-fluoro 7-(2-imidazolinyl)bicyclo[4.2.0]1,3,5-octatriene is obtained by replacing 3-chloro 7-cyano bicyclo[4.2.0]1,3,5-octatriene with 4-fluoro 7-cyano bicyclo[4.2.0]1,3,5-octatriene.

m.p.=98°–103° (base); 181°–185° (fumarate).

| Analysis (fumarate) | C % | H % | N % |
|---|---|---|---|
| Calculated | 58.82 | 4.93 | 9.14 |
| Found | 58.51 | 4.93 | 9.03 |

EXAMPLE 12

4-sulphamoyl 7-(2-imidazolinyl)bicyclo[4.2.0]1,3,5-octatriene

Step A:

4-sulphamoyl 7-cyano bicyclo[4.2.0]1,3,5-octatriene.

The conditions of the MEERWEIN reaction (diazotation with NaNO$_2$ in concentrated hydrochloric acid, then treatment with a suspension of CuCl$_2$ in an acetic acid solution of SO$_2$) are applied to 10 g of 4-amino 7-cyano bicyclo[4.2.0]1,3,5-octatriene to obtain the corresponding sulphochloride, which, when treated immediately with a concentrated ammonia solution, gives 2.2 g of 4-sulphamoyl 7-cyano bicyclo[4.2.0]1,3,5-octatriene (recrystallised from methanol).

m.p.=200°-203° C.

Step B:

4-sulphamoyl 7-(2-imidazolinyl)bicyclo[4.2.0]1,3,5-octatriene.

2.9 g of 1,2-diamino ethane and 2 g of 4-sulphamoyl 7-cyano bicyclo[4.2.0]1,3,5-octatriene obtained in Step A above, are added to 10 ml of methanol. This mixture is then saturated in $H_2S$ while maintaining the temperature at 0° C. and refluxed for 4 hours. By evaporation of the solvent 3 g of brown oil are obtained which are recrystallised into 5 ml of acetonitrile. After a new recrystallisation in methanol, 1.1 g of 4-sulphamoyl 7-(2-imidazolinyl)bicyclo[4.2.0]1,3,5-octatriene are obtained.

m.p.=200° (decomposition).

IR: $NH_2$ bands: 3300 and 3380 cm$^{-1}$, 1620 cm$^{-1}$. NH bands: 3100 to 2000 cm$^{-1}$, $SO_2$ bands: 1160 and 1330 cm$^{-1}$.

PHARMACOLOGICAL STUDY OF THE COMPOUNDS OF THE INVENTION

The compounds of the invention were tested on peripheral and central α-adrenoreceptors in comparison with conventional reagents: cirazoline(α-agonist), azepexole(α-agonist), clonidine($\alpha_1$- and $\alpha_2$-agonist) and "ST587" ($\alpha_1$-agonist), on peripheral receptors ("vas deferens") and central receptors (sleep in chicks).

For example, in pithed rats, the compound of Example 1 and also its isomers, when administered in a dose of 1 mg/kg i.v., compete significantly with the effect of cirazoline, a fairly specific $\alpha_1$-agonist (Lefevre et al., Eur. J. Pharmacol. 43, 85; 1977).

The same type of experiment was carried out with "ST587", viz. 2-(2-chloro-5-trifluoromethylphenylimino)imidazoline, a selective $\alpha_1$-agonist (De JONGE et al., Life Science, vol. 28, 2009-2016; 1981). These results show that the compounds of the invention are capable of antagonising the post-synaptic $\alpha_1$-adrenoreceptors of the rat.

A study carried out in comparison with a selective $\alpha_2$-agonist, azepexole or 2-amino-6-ethyl 5,6,7,8-tetrahydro-4H-oxazolo[4,5-d]azepine, dihydrochloride (Timmerman and Van Zwieten, Eur. J. Pharmacol. 63, 199-202; 1980) has shown that the compounds of the invention (racemic form and isomers) are very effective at a dose of 1 mg/kg i.v. in pithed rats.

The results obtained in comparison with clonidine on the two types of adrenoreceptors (more on $\alpha_2$) concur with the previous studies. In chicks, the compound of the invention, at a dose of 1 mg/kg i.v., causes inhibition of sleep induced by clonidine at a dose of 0.750 mg/kg.

Finally, in dogs anaesthetised with nembutal and subjected to artificial respiration, it was found that the compounds reverse the hypertensive effects of adrenaline and reduce those of noradrenaline.

The above experiments show that the compounds of the invention are effective on $\alpha_1$ and $\alpha_2$-adrenoreceptors, the isomers being more especially selective with regard to the one or the other of these receptors.

They can therefore be used therapeutically in the treatment of ailments and/or conditions which are adrenoreceptor-related, such relationship being well known in the art.

The compounds of the invention can be administered orally or parenterally at a daily dose of from 0.1 to 1 mg/kg. The compositions that may be administered orally (tablets, dragées, soft gelatin capsules, . . . ) may contain, for example, from 5 to 50 mg of active ingredient and also conventional pharmaceutical excipients, such as lactose, starch, talc . . . Compositions for parenteral administration preferably contain a unit dose of from 5 to 25 mg of active ingredient in the form of an addition salt in aqueous solution.

For example, the compositions may be in the form of soft gelation capsules containing 10 mg of the tartrate of the compound of Example 1 and 40 mg of lactose.

We claim:

1. A bicyclo[4.2.0]1,3,5-octatriene selected from those corresponding to the formula:

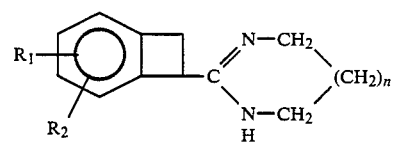

in which:
$R_1$ and $R_2$ each represent hydrogen, halogen, alkyl and alkoxy, each having from 1 to 4 carbon atoms inclusive, sulphonamide possibly substituted by an alkyl having from 1 to 4 carbon atoms inclusive; or together represent methylenedioxy, n is 0 or 1, in racemic form or as an optical isomer thereof, or an addition salt thereof with a pharmaceutically acceptable acid.

2. A compound of claim 1 in which $R_1$ and $R_2$ each represent hydrogen.

3. A compound of claim 1, which is selected from (d,l) 7-(2-imidazolinyl)bicyclo[4.2.0]1,3,5-octatriene, its d and l isomers, and their salts of addition with a pharmaceutically acceptable acid.

4. A method for treating a living animal body afflicted with a condition which is related to adrenoreceptor activity, which comprises the step of administering to the said living animal an amount of a compound of claim 1, which is effective for the alleviation of the said condition.

5. A pharmaceutical composition, useful for alteration of adrenoreceptor activity, containing as active principle an effective amount of a compound of claim 1 together with a pharmaceutically acceptable diluent or carrier.

6. A pharmaceutical composition, useful for alteration of adrenoreceptor activity, containing as active principle an effective amount of a compound of claim 2 together with a pharmaceutically acceptable diluent or carrier.

7. A pharmaceutical composition, useful for alteration of adrenoreceptor activity, containing as active principle an effective amount of a compound of claim 3 together with a pharmaceutically acceptable diluent or carrier.

8. A method for affecting the alpha 1 or alpha 2 adrenoreceptors in a subject in need of alteration of the same which comprises the step of administering to said subject an adrenoreceptor activity altering amount of a compound of claim 1.

* * * * *

UNITED STATES PATENT AND TRADEMARK OFFICE
CERTIFICATE OF CORRECTION

PATENT NO. : 4,567,181

DATED : January 28, 1986

INVENTOR(S) : Charles Malen, Jean-Louis Peglion, Michel Laubie and Jean-Claude Poignant It is certified that error appears in the above-identified patent and that said Letters Patent is hereby corrected as shown below:

Title Page, between [63] Related U.S. Application Data and [51]; insert -- [30] Foreign Application Priority Data
Jan. 14, 1983 [FR] France . . . . 83-00502 --
(Declaration and Power of Attorney and Notice of Allowability dated August 13, 1985 - paper number 6)

Title Page [56] References Cited, U.S. PATENT DOCUMENTS; insert this as the first line; -- 3,879,415 4/75 Matlesics, et al. . . . 548/347 --
(attachment to paper #4 - PTO 1449)

Title Page [56] References Cited, OTHER PUBLICATIONS, line 1; after "Gilman" insert a comma -- , --

Col. 1, line 23; "form" should read -- from --

Col. 2, line 39; "7-yano" should read -- 7-cyano --

Col. 3, line 13; "-tartarate" should read -- -tartaric --

Col. 3, line 13; "-tartaric" should read -- -tartrate --

Signed and Sealed this

Tenth Day of June 1986

[SEAL]

Attest:

DONALD J. QUIGG

Attesting Officer    Commissioner of Patents and Trademarks